(12) United States Patent
Freiburger

(10) Patent No.: US 8,696,577 B2
(45) Date of Patent: Apr. 15, 2014

(54) TONGUE IMAGING IN MEDICAL DIAGNOSTIC ULTRASOUND

(75) Inventor: Paul Donald Freiburger, Seattle, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 13/452,546

(22) Filed: Apr. 20, 2012

(65) Prior Publication Data

US 2013/0281856 A1 Oct. 24, 2013

(51) Int. Cl.
*A61B 8/00* (2006.01)

(52) U.S. Cl.
USPC .............................. 600/443; 600/407; 600/437

(58) Field of Classification Search
USPC .......................................... 600/407, 437, 443
See application file for complete search history.

(56) References Cited

U.S. PATENT DOCUMENTS 5,479,926 A * 1/1996 Ustuner et al. ................ 600/440
5,899,863 A * 5/1999 Hatfield et al. ............... 600/443
6,149,594 A * 11/2000 Rock et al. .................... 600/437

OTHER PUBLICATIONS

B. Bernhardt et al., "Ultrasound as visual feedback in speech habilitation: Exploring consultative use in rural British Columbia, Canada," Clinical Linguistics & Phonetics, vol. 22(2), pp. 149-162, Feb. 2008.
B. Bernhardt et al., "Ultrasound in speech therapy with adolescents and adults," Clinical Linguistics & Phonetics, vol. 19(6/7), pp. 605-617, Sep.-Nov. 2005.
B. Bernhardt et al., "Speech habilitation of hard of hearing adolescents using electropalatography and ultrasound as evaluated by trained listeners," Clinical Linguistics & Phonetics, vol. 17(3), pp. 199-216, 2003.
M. Adler-Bock et al., "The Use of Ultrasound in Remediation of North American English /r/ in 2 Adolescents," American Journal of Speech-Language Pathology, vol. 16, pp. 128-139, May 2007.
Interson Corporation, Software Installation Instructions & Quick Start Guide, 2008-2011.
Interson Medical Instruments, "SeeMore™ User Guide," 2008-2011.

* cited by examiner

*Primary Examiner* — Peter Luong

(57) ABSTRACT

Tongue imaging is provided in medical diagnostic ultrasound. Ultrasound data is processed to enhance the information from the tongue. The enhancement increases signal from the tongue, decreases other signals, or both. The resulting image may more clearly present the tongue or tongue surface for feedback to a patient or review by a speech therapist.

20 Claims, 2 Drawing Sheets

TONGUE IMAGING IN MEDICAL DIAGNOSTIC ULTRASOUND

BACKGROUND

The present embodiments relate to tongue imaging.

The "R" sound is one of the most common speech defects (vocalic R speech disorder) in children, and one of the hardest to correct. A significant number of children who struggle with the "R" sound go to a speech pathologist weekly for a couple of years, make no progress, and then get discharged from therapy with a conclusion of "unlikely to ever learn it."

Ultrasound imaging may be used to improve speech pathology. Ultrasound imaging is used as biofeedback to improve outcome, shorten treatment times, and save money for schools. Portable ultrasound devices scan the mouth to show a patient how they are incorrectly positioning their tongue. For example, to guide the patient, a speech pathologist may use a pen as a pointer on the screen to give the patient a target to aim at in curling their tongue while pronouncing "R"s. This biofeedback based on ultrasound imaging may increase the therapy success rate for "R," "L," "D," "T," and "N" speech disorders, and possibly many others.

However, ultrasound biofeedback for speech therapy may be difficult for some patients. Ultrasound scanning generates speckle noise and includes signals from other objects than the tongue. A patient may find it difficult to visualize the tongue from an ultrasound image. The speech pathologist may not be well trained in ultrasound scanning, so may have difficulty configuring the ultrasound system.

BRIEF SUMMARY

By way of introduction, the preferred embodiments described below include methods, systems and computer readable media for tongue imaging in medical diagnostic ultrasound. Ultrasound data is processed to enhance the information from the tongue. The enhancement increases signals from the tongue, decreases signals from other objects, or both. The resulting image may more clearly present the tongue or tongue surface for feedback to the patient or speech pathologist.

In a first aspect, a method is provided for tongue imaging in medical diagnostic ultrasound. An ultrasound transducer is positioned to scan a tongue of a patient. The tongue of the patient is scanned with the ultrasound transducer. Data is acquired from the scanning. The data represents a mouth, including the tongue, of the patient. The data is processed to increase return of the tongue relative to other signals from the mouth of the patient represented by the data. A sequence of images of the tongue from the processed data is displayed. The sequence of images shows movement of the tongue.

In a second aspect, a non-transitory computer readable storage medium has stored therein data representing instructions executable by a programmed processor for tongue imaging in medical diagnostic ultrasound. The storage medium includes instructions for obtaining ultrasound data representing a tongue, increasing, by image processing, a distinction between a surface of the tongue and other structure represented in the ultrasound data, and displaying an image of the surface of the tongue.

In a third aspect, a system is provided for tongue imaging in medical diagnostic ultrasound. A receive beamformer is operable to receive ultrasound data from a scan of a patient using an ultrasound transducer. An image processor is configured to maintain tongue information in the ultrasound data and to suppress signals other than the tongue information and noise in the ultrasound data. A display is operable to display an image of a tongue as a function of the ultrasound data output by the image processor.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Ultrasound is used to image the tongue, such as the surface of the tongue. Tongue imaging may be used in studying chewing, providing feedback in speech therapy, and/or other applications. These applications may benefit from an image enhanced to show the tongue, such as a top surface of the tongue, with more distinction from other tissues or noise. The top surface of the tongue is a bright reflector in B-mode imaging due to the tissue/air interface. Since anything in the image besides the tongue or tongue surface is extraneous for these applications, the tongue and/or tongue surface may be further enhanced relative to other signals.

Image processing may enhance the image of the surface of the tongue or other portion of the tongue. The enhancement is performed by increasing brightness of the desired information and/or suppressing the undesired information (e.g., suppressing noise and signals from objects other than the tongue or surface in the image).

Figure 1:
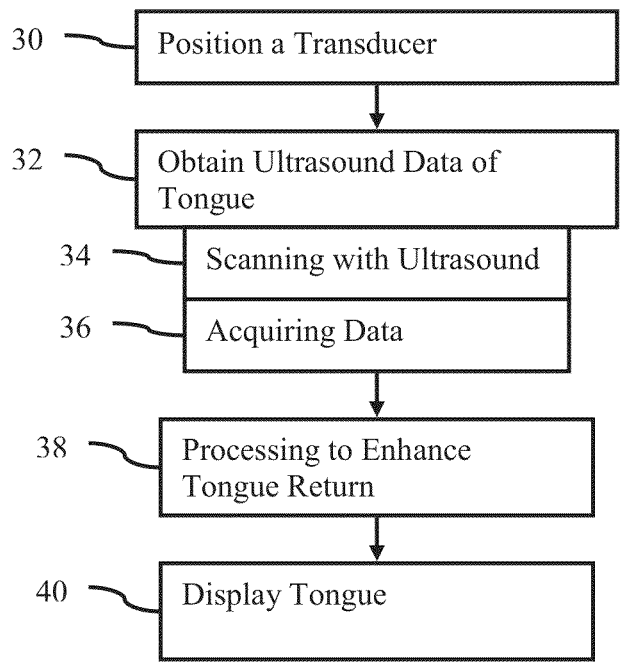
FIG. 1 is a flow chart diagram of one embodiment of a method for tongue imaging in medical diagnostic ultrasound.

FIG. 1 shows a method for tongue imaging in medical diagnostic ultrasound. The method is implemented by a medical diagnostic ultrasound imaging system, a review station, a workstation, a computer, a PACS station, a server, combinations thereof, or other device for processing ultrasound data. For example, the ultrasound system shown in FIG. 4 implements the method. In one embodiment, a portable ultrasound system is used, such as a handheld ultrasound system, a laptop computer with a transducer/beamformer attachment, or a briefcase type ultrasound system.

The method is implemented in the order shown or a different order. Additional, different, or fewer acts may be performed. For example, acts 30 and/or 34 are not performed and the ultrasound data is instead acquired from a memory (e.g., the scanning is performed by a different device and/or user at a different time). As another example, the display of an image in act 40 is not performed. In another example, graphics or other feedback information are added to the displayed image.

In act 30, an ultrasound transducer is positioned. The ultrasound transducer includes one element or an array of elements, such as a one or two-dimensional array of elements.

The transducer is in a handheld probe housing. In other embodiments, the transducer is in an intracavity probe, such as a probe adapted in size and shape for insertion within a mouth of a patient.

Figure 2:
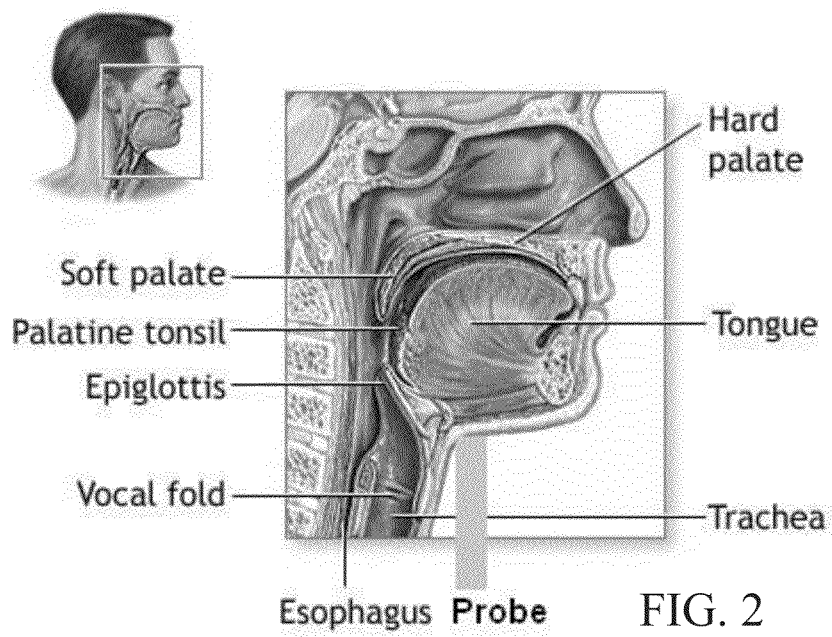
FIG. 2 illustrates anatomy and an example probe position for tongue imaging according to one embodiment.

The ultrasound transducer is positioned by a user. The user is a patient, a speech therapist, an aid or other person. The user holds the transducer against or in the body of the patient. FIG. 2 shows the probe with the transducer positioned against the skin of a patient below the chin or mouth and directed upwards to scan the mouth. The probe is placed near the neck and directed towards the mouth. Other positions of the probe, such as against a check, may be used.

For a one-dimensional array or wobbler, the probe is also oriented. If the longitudinal cross-section of the tongue is to be scanned, the direction of wobble or the longitudinal direction of a one-dimensional array is oriented to be parallel with the longitudinal axis of the tongue. Other orientations may be used, such as for planar scanning of the short axis of the tongue.

In an alternative embodiment, the user positions the transducer, but uses glue, straps, or a fitting to hold the transducer against or in the body of the patient. Robotic positioning may be used. Rather than moving the transducer, the patient may place their body (e.g., the chin or skin below the mouth) on a stationary transducer.

The position is to scan the tongue of the patient. Any position for scanning the tongue is provided. The tongue may be scanned longitudinally, perpendicularly to the longitudinal axis (e.g., short axis), or other direction. For speech therapy with an "R" sound, the longitudinal axis is scanned. The scan plane is a center cross section along the longitudinal axis. For the "SH" sound, the tongue is imaged in the short axis (e.g., laterally).

In act 32, ultrasound data is obtained. The ultrasound data is obtained during real-time imaging, such as obtaining data as a patient is scanned. Alternatively, the ultrasound data is obtained from a memory, such as obtaining the data from a database of images, a patient record, or a transfer from another device. The ultrasound data is formatted for display on a display device or in another format, such as a polar coordinate or other acquisition format. The data is obtained by requesting the data, loading the data, receiving the data, recording the data, or other process.

For the real-time implementation, the ultrasound data is obtained by scanning the patient. Acoustic energy is transmitted along one or more beams. One transmission may be used to scan along one or more lines. To scan an area, one or more transmissions are used. For example, a plurality of transmit beams in a linear, sector, or Vector® format are used. To scan a volume, the transmit beams are steered in azimuth and elevation. Electronic or mechanical steering may be used. For area or volume scans, the transmissions may occur sequentially along different scan lines.

The transmitted acoustic energy passes from the transducer into the patient. Some or all of the acoustic energy may reflect from tissue or other structures in the patient. The acoustic energy reflected back to the transducer is received by the transducer. Based on the propagation time, the location and magnitude of the reflection may be detected. Receive beamforming is performed to sample the scan region. The receive beams are formed in response to transmissions along the same or different scan lines as the transmit beams.

By repeating the transmission and reception, the patient is scanned in act 34. The same line, area, or volume may be repetitively scanned to acquire ultrasound data representing the region at different times. The repetition of the scanning of the same region provides data for a sequence of images of the tongue. Alternatively, data for a single image of the tongue is acquired by scanning.

The beamformed data from the scanning is processed or stored. The scanning results in acquiring the ultrasound data in act 36. Alternatively, the data is acquired from a previous scan, memory, or transfer.

The acquired ultrasound data is pre-detected data or detected data. For example, the acquired ultrasound data is B-mode data representing the intensity of the acoustic echoes. As another example, the acquired ultrasound data is Doppler or color data, such as Doppler tissue data representing a velocity, variance, or energy associated with movement. Other modes of detection may be used, such as harmonic.

The ultrasound data is obtained without processing, such as raw data output by a receive beamformer. Some processing may be provided, such as receiving data output by a detector or estimator without further processing. Alternatively, the ultrasound data is processed, such as spatially or temporally filtered. The ultrasound data may or may not be scan converted.

By having positioned the transducer to scan the tongue, the ultrasound data represents the tongue, other tissue, bone (e.g., jaw and/or teeth), fluid, air, and/or noise. For one-dimensional scanning, the different types of signal returns along the line include returns from the tongue for a line. For two or three-dimensional scanning, the different types of signal returns for area or volume samples include returns from the tongue. Depending on the position of the transducer, the sample line, plane, or volume may be positioned to include all or different parts of the tongue. In one embodiment, the data represents returns from a plane along a cross-section of the longitudinal axis of the tongue. In another embodiment, the data represents returns from a plane along a short-axis of the tongue.

In act 38, the ultrasound data is processed. The processing increases the value of data at locations for the tongue relative to other values for other objects represented by the data. The increase may be provided by decreasing values associated with echoes from other than the tongue. Alternatively or additionally, the increase is by increasing the values associated with the tongue. The relative increase better distinguishes the tongue from other tissue, fluid, bone, noise and/or other objects. The distinction between the tongue and other information is increased. This increase is of the difference between values. For example, the difference between values for locations associated with the tongue and other locations is increased from an average of 50 to an average of 100 on a 0-255 scale. Other differences may be provided, such as eliminating values not associated with the tongue. Image processing is used to enhance the image of the tongue in ultrasound imaging.

The distinction or increase may be between values at locations for the tongue and all other locations. In other embodiments, signals at some but not all locations are reduced relative to the tongue. For example, values representing teeth, lips, or other portions of the mouth used in speech may also be enhanced or may not be reduced relative to the values representing the tongue.

The enhancement may be for the entire tongue or a portion of the tongue. For example, the top surface of the tongue is enhanced. Top is relative to a patient when standing up with their tongue in an at rest position. The locations of interest are the generally bright regions (e.g., high intensity) associated with the tongue/air interface on the surface of the tongue. In other embodiments, the muscle of the tongue is enhanced. The tip, sides, edges, back, or other portions of the tongue may be enhanced. The values for portions of the tongue not being enhanced may be reduced or eliminated, such as reducing the values as is done for other non-tongue objects.

The processing is implemented during acquisition or after data acquisition on stored data. The processing may operate on previously displayed images or on data to be used to display an image. The processing is image processing whether operating on display (e.g., RGB) values in a display format (e.g., Cartesian format) or on values in the ultrasound pipeline (e.g., polar coordinate, B-mode intensity values).

The values for the locations associated with the tongue are increased relative to values for other locations using one, two, or more processes. Rather than relying on a relative greater acoustic echo from the tongue surface, further processing enhances the tongue. Only one process is used, or combinations of multiple processes are used.

In one embodiment, thresholding is applied. The threshold is selected to include most or all values associated with the tongue while not including values for other locations. Since the values associated with the tongue surface are likely greater than values associated with at least some other locations, thresholding may identify values to maintain or increase and/or values to remove or decrease. For example, intensities below the threshold are decreased by any amount. These intensities may be replaced with a zero value or a value for a noise floor. Alternatively or additionally, the values above the threshold are increased. Any linear or non-linear mapping may be used.

Prior to thresholding, the ultrasound data may be spatially filtered. By applying a low pass filter, locations associated with the tongue may have their values more likely increased to be above the threshold and peak noise values may more likely have their values decreased to be below the threshold. Directional or gradient filtering may be used based on the expected direction of the tongue.

Where other tissue or structures are associated with values likely above the threshold, these tissue or structures may be masked. For example, any values for locations in the near field (e.g., 1-3 cm closest to the transducer) may be masked, removed, or decreased prior to or after thresholding.

Another process is persistence. In an ongoing sequence of scans and associated frames of data, data representing the same locations at different times may be temporally filtered. Any filtering may be used, such as infinite impulse response or finite impulse response filtering. Persistence may remove high value signals due to noise or other variation more rapid than movement of the tongue. Where the frame rate (e.g., scan rate) is sufficiently high (e.g., 20 Hz) relative to tongue movement, persistence may remove values associated with noise while maintaining values associated with the tongue. The persistence is applied in a moving window of any number of frames, such as 2-4 frames of data where each frame of data represents the mouth at a different time. The number of frames is selected in light of the frame rate to avoid motion blurring due to movement of the tongue.

Another process is spatial compounding. Frames of data with different spatial response for the same locations are obtained. For example, different steering is used for each scan and associated frame of data. In a linear scan format, two or more (e.g., three) frames with different steering (e.g., +/−10 degrees and normal to the transducer) are obtained. The frames represent part of the mouth in an overlap region. Locations in the overlap region are insonified from different directions by the different steering. By combining the values from the different frames for the same location, spatial compounding is provided.

The spatial compounding may provide temporal filtering or persistence. The spatial diversity without persistence may reduce values associated with noise or soft tissue, resulting in enhancing values associated with the tongue, such as the tongue surface.

Another process similar to spatial compounding and persistence is frequency compounding. The same locations are scanned using different imaging frequencies. The frequency of the acoustic waveform transmitted to scan may be different at different times or for different frames of data. Alternatively or additionally, the frequency used for receiving the echoes may be different for different times or different frames of data. For example, received signals are separated into harmonic (e.g., second harmonic) and fundamental response. After detection, the frames of data from these different frequencies may be combined. Pre-detection combination may be used.

Combining data associated with different frequencies and representing the same locations reduces noise. This increase in the relative values for the locations associated with the tongue may better distinguish the tongue locations from other locations.

Yet another process is high pass filtering. Any high pass filter with any desired cut-off frequency may be used. For example, a Gaussian filter with a one, two, or three-dimensional kernel (e.g., 10×10) is applied to a frame of ultrasound data. The filtering may be directional, such as filtering to distinguish relatively rapid change more in the vertical or depth direction than in the horizontal or azimuth direction in two-dimensional scanning. Given the probe orientation in FIG. 2, such directional filtering is oriented relative to the likely position of the top surface of the tongue.

High pass filtering reduces values surrounded by similar values. Since the top surface of the tongue is associated with a change from higher values to lower values, the top surface is enhanced relative to surrounding regions. Since noise and teeth surface may have a high frequency response as well, further masking or filtering may be provided.

Masking is another process. The values for some locations may be increased or decreased. Given a known or expected placement of the transducer, the locations associated with the tongue may occur within a given range of depths from the transducer. By masking the near field and/or the far field, locations associated with other objects (e.g., tissue, fluid or bone) may be reduced while not reducing locations associated with the tongue. Lateral masking may be used. The masking may adapt to a depth of scan or field of view setting and/or a measurement of the patient (e.g., chin to nose, head diameter, or head circumference).

In one embodiment, unsharp masking is used. Rather than or in addition to masking based on location, the processed data is formed by combining low resolution and high resolution data. First, a low resolution copy of the data is generated through low pass filtering. Second, a copy of the data with a different resolution is generated, such as by using the original data or high pass filtering. The two frames of relatively high and low resolution data are combined linearly or non-linearly. The resulting data has enhanced edges and a smoother background. This produces a sharper representation of the surface of the tongue with less background noise.

Different amounts of reduction may be provided for different regions or ranges by combining the low resolution and high resolution data in different ways. For example, weighting the lower resolution data less than the higher resolution data less will provide less background smoothing but possibly a sharper image of the surface of the tongue.

Another process is edge detection. Using linear filtering from various directions, gradient calculation, correlation, thresholding, template matching, modeling, or other approaches, edges may be identified from the ultrasound data. In one embodiment, spatial variance of the values of a frame is calculated. Any variance may be used, such as a difference between a square of a mean and a mean of the square of the values. The spatial variance may indicate a type of tissue. For example, soft tissue generally is at about 5.57 dB. Tissue structures, such as the top surface of the tongue, may have greater variance or standard deviation. Using the variance, locations associated with the tongue may be distinguished from other locations. The values for the different locations may be increased and/or decreased to enhance the data from the tongue.

The detected edges may be low pass filtered or a curve fitted to better define the edge. Edge detection may use template matching. An expected or likely tongue or tongue surface shape (e.g., curve or surface) is matched to the data. Any edges sufficiently close using any cost function may be identified as the edge in the ultrasound data.

By identifying the locations of an edge or edges associated with the tongue, the values representing the tongue may be relatively increased. The values at the locations may be maintained while values for other locations are reduced or eliminated. The ultrasound data may be replaced with a line or surface for the edge.

Another approach is segmentation. Using variance, relative locations, feature detection, pattern matching or other approaches, different types of objects represented by the data are distinguished. Soft tissue, bone, anatomical structures, fluid, and air may be distinguished. The tongue is segmented from other objects. The locations associated with the tongue or portion of the tongue are segmented from locations associated with other objects. To enhance the tongue locations, values are increased and/or decreased based on the object or segmentation.

In another process, tracking is performed. The locations associated with the tongue are identified, such as automatically by a processor (e.g., edge detection) or manually by a user. For subsequent frames of ultrasound data, correlation (e.g., cross-correlation, sum of absolute differences, or other similarity measure) is performed between frames of data. The tongue in one frame is located based on the offset associated with the greatest correlation from another frame.

In act 40, an image is displayed. The ultrasound data, a fit model, identified lines, or other information representing the tongue identified from the ultrasound data is used to generate the image. For example, the values for various locations are mapped to red, green, blue (RGB) values for display. As another example, the adjusted intensity values are mapped to grey levels.

The format of the ultrasound data or other information may be converted. Where the data to be displayed is in a different format, such as polar coordinate format, than the screen, the format is changed. The data is scan converted to a Cartesian coordinate or other screen format.

The image data is output to a display. A display buffer or other memory outputs the image data. The image is of the tongue with or without other information. Text, graphics, or other information may be added. A graphical overlay may be added. Targets or application specific graphics may be added. For example, points, arrows, lines, curves, targets, or icons indicating a desired tongue position may be included in the image. As another example, a graphic for teeth may be added in order to provide a reference.

Using either added graphics or the mapping of display values, the locations associated with the tongue may be enhanced. Rather than or in addition to changing the relative levels of the values, the locations associated with the tongue are enhanced by creation of the image. The tongue locations may be mapped to color values and other locations mapped to gray scale. A graphic overlay in white, color, or grey may be presented over the tongue locations and not other locations.

The image is a one, two, or three-dimensional representation. For a one-dimensional representation, an M-mode type display may be used. The intensities along a line are shown over time. For a given line on the display image, the intensities at one time for the line are mapped to display values. For a two-dimensional representation, the image represents the area or plane of the scan. The two-dimensional display is mapped to spatial locations. For a three-dimensional representation, the data representing a volume is rendered to a two-dimensional image. Any rendering may be used, such as surface or projection rendering. A viewing direction is assigned and the data is rendered based on the viewing direction. Any viewing direction may be used, such as from a side or perspective view of the tongue.

The image represents the tongue. Where the tongue surface (e.g., top of tongue) is enhanced, the image represents the top surface portion of the tongue. Due to the processing, the tongue is distinguishable from other objects to a greater extent than without the processing. The relative difference highlights the tongue or makes the tongue more visible to the user. In the speech therapy application, the image depicts the tongue as the patient speaks for feedback to the patient. Since the image displays the tongue more clearly or to a greater extent than other objects, the feedback may be more effective and less confusing to the patient and/or speech therapist.

The image is statically displayed. The one image is displayed for any period. In other embodiments, the image is one of a sequence of on-going images. The sequence of images may show movement of the tongue. The images representing the tongue at different times are displayed in time sequence. By repeating acts 32-40, a sequence of images is generated.

The images in the sequence are processed in act 38 independently. Alternatively, data or images for one image in the sequence are used in the processing of another image. Using temporal filtering (e.g., persistence), tracking, or other process, data from different times may be used to enhance the values at locations for the tongue in another time. A moving window may be used where a given frame of data is used for generating multiple images.

Figure 3:
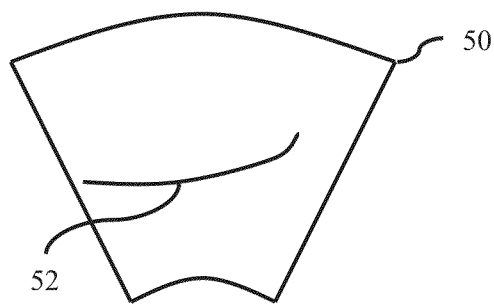
FIG. 3 is an example image of a tongue surface in cross-section.

By showing the position of the tongue over time (e.g., movement of the tongue), the use of the tongue by the patient may be analyzed. For speech therapy, the positioning of the tongue for making a particular sound may be viewed. For example, to correctly make an "R" sound, the tip of the tongue should curl upwards. FIG. 3 shows an example image 50 with the tongue 52 represented as a line either from ultrasound data or a curve fitted to the ultrasound data. The displayed tongue may be monitored visually for this curl. Automated feedback, such as a measure of the amount of curl, timing of the tongue movement, or other characteristic may also provide information to the patient or speech therapist.

Any frame rate may be used for the images. In one embodiment, the frame rate is at least 20-30 Hz, providing little to no perceived jumping or jerkiness. Real-time imaging is perceived. Lesser frame rates may be provided.

The image is of any size. In one embodiment, the image is displayed on a 4×6 inch or other handheld display screen. For more convenient or clear feedback, the image may be displayed on a 13 inch or greater display. Larger display may allow for easier visualization.

Figure 4:
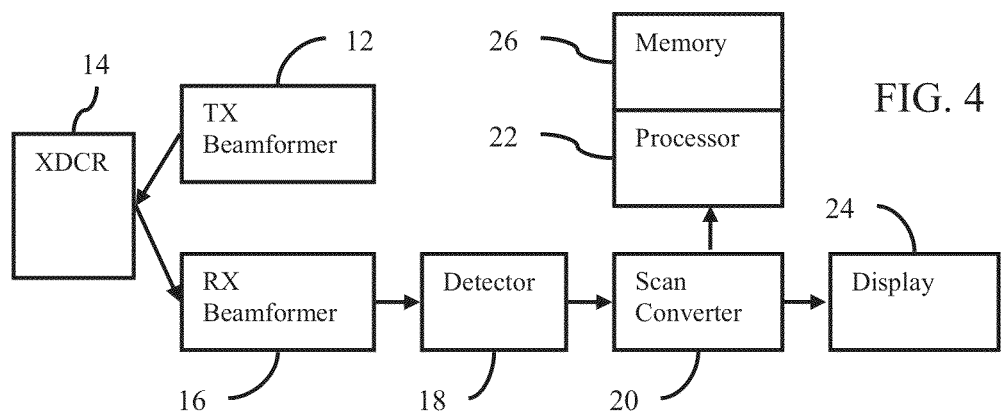
FIG. 4 is a block diagram of one embodiment of a system for tongue imaging in medical diagnostic ultrasound.

FIG. 4 shows one embodiment of a system for tongue imaging in medical diagnostic ultrasound. The system is a medical diagnostic ultrasound imaging system, but may be a computer, workstation, database, server or other system. In one embodiment, the system is a cart-based (e.g., housing with wheels, keyboard, and monitor with a releasably connectable transducer probe assembly) ultrasound imaging system. A tongue imaging application is loaded onto or run by the system. In another embodiment, the system is a handheld ultrasound imaging system. The transducer, processing electronics, and/or display of the handheld system may be worn or carried by the operator. For example, a probe is held in one hand and a display is held in another hand with the electronics in one or both components. In yet another embodiment, the system is a laptop or briefcase system. For example, a transducer probe with beamformer electronics in the probe connects with a laptop computer, such as through a USB connection. The laptop computer performs processing and generates the image.

The system includes a user interface. A simple user interface may be provided. For example, the user merely selects a tongue imaging application. Any beamformer or processing parameters are established based on the selection. Additional or different inputs may be provided, such as inputs for setting gain, selecting processing, setting dynamic range, setting depth, and setting frequency. Alternatively, more complex user interfaces may be used, such as associated with cart-based ultrasound systems.

The system 10 includes a transmit beamformer 12, a transducer 14, a receive beamformer 16, a detector 18, a scan converter 20, a processor 22, a display 24, and a memory 26. Different, fewer or additional components may be provided. For example, an offline workstation implements the processor 22, memory 26, and display 24 without the additional ultrasound acquisition components. As another example, the scan format used is linear and samples at a density of the display 24 so that a scan converter 20 is not provided. In yet another example, a user input is provided.

The ultrasound transducer 14 comprises an one- or multi-dimensional array of piezoelectric, ceramic, or microelectromechanical elements. In one embodiment, the transducer 14 is a one-dimensional array of elements for use as Vector®, linear, sector, curved linear, or other scan format now known or later developed. The array of elements has a wavelength, half wavelength, or other sampling frequency, such as spacing for 1-10 MHz transducer (e.g., 3 MHz or 7.5 MHz). A half-wavelength sampling of elements allows for greater steering angles, providing a larger field of view for imaging the tongue of adults. In an alternative embodiment, a single element is provided. Mechanical steering, such as associated with a wobbler is used for scanning along two or three-dimensions. A wobbler may be used with a one-dimensional array for volume scanning.

The transducer 14 is adapted for use external to or use within the patient. For example, the ultrasound transducer 14 is in a handheld probe with a housing sized and shaped to fit in a hand of the user while positioned near the mouth. As another example, the ultrasound transducer 14 is part of an intracavity probe, such as a housing with a rounded cylindrical extension for insertion into the mouth and housing the elements and a handle portion for holding by the user. In another example, the ultrasound transducer 14 is within a chin, head, or other holder for placement against the patient by the patient resting their body on the holder. Multiple spatially distributed transducers or even scanning systems may be employed.

The transmit and receive beamformers 12, 16 operate as a beamformer. The beamformer is operable to acquire electronically or mechanically steered frames of data using the ultrasound transducer 14. The scan pattern is in any format, such as along a single scan line for one-dimensional scanning, in sector, Vector® or linear for two-dimensional scanning, or in a three-dimensional format. Any size field of view may be used, such as a sector or Vector® field of view over a 75 degree or 90 degree range.

The transmit beamformer 12 is one or more waveform generators for generating a plurality of waveforms to be applied to the various elements of the transducer 14. By applying relative delays and apodizations to each of the waveforms during a transmit event, a scan line direction and origin from the face of the transducer 14 is controlled. The delays are applied by timing generation of the waveforms or by separate delay and/or phasing components. The apodization is provided by controlling the amplitude of the generated waveforms or by separate amplifiers.

To scan a region of a patient, electrical waveforms generated by the transmit beamformer 12 are provided to elements of the ultrasound transducer 14. In response, the waveforms are transduced into acoustic energy, which is transmitted sequentially along each of a plurality of scan lines. In alternative embodiments, acoustic energy is transmitted along two or more scan lines simultaneously or along a plane or volume during a single transmit event.

The receive beamformer 16 comprises delays and amplifiers for each of the elements in the receive aperture. Acoustic echoes impinge upon the ultrasound transducer 14, which converts the acoustic energy into electrical receive signals. The receive signals from the elements are relatively delayed and apodized to provide scan line focusing similar to the transmit beamformer 12, but may be focused along scan lines different than the respective transmit scan line. The delayed and apodized signals are summed with a digital or analog adder to generate samples or signals representing spatial locations along the scan line. Using dynamic focusing, the delays and apodizations applied during a given receive event or for a single scan line are changed as a function of time. Signals representing a single scan line are obtained in one receive event, but signals for two or more scan lines may be obtained in a single receive event. A frame of data is acquired by scanning over a complete pattern with the beamformer. In alternative embodiments, a Fourier transform or other processing is used to form a frame of data by receiving in response to a single transmit.

The detector 18 is a B-mode detector, Doppler detector or other detector. The detector 18 detects intensity, velocity, energy, variance or other characteristic of the signals for each spatial location in the frame of data. The detector 18 may include a filter, such as for obtaining information at a harmonic of the transmit frequency. A buffer, adder, corner turning memory, or other components may be provided for combining data from different times to detect.

The scan converter 20 comprises a processor, filter, application specific integrated circuit or other analog or digital device for formatting the detected data from a scan line format (e.g., polar coordinate format) to a display or Cartesian coordinate format. The scan converter 20 outputs each frame of data in a display format. In one embodiment, each frame has the same number of pixels and an associated image geometry corresponding to the display.

The processor 22 is one or more memories, general processors, control processors, digital signal processors, application specific integrated circuits, filters, multiplexers, multipliers, adders, lookup tables, graphics processing units, or combinations thereof. In one embodiment, the processor 22 is a personal computer, motherboard, graphics processing unit, separate circuit board or other processor for image processing using transfers of data to and from the ultrasound image generation pipeline or processing path (i.e. receive beamformer 16, detector 18, scan converter 20 or display 24). In other embodiments, the processor 22 is part of the image generation pipeline.

The processor 22 is a collection of devices for processing data or is programmed to process the data. The processor 22 is configured by hardware and/or software to process ultrasound data for enhancing tongue information relative to other information. The processor 22 is an image processor for distinguishing tongue information from some or all other information. The image processor may operate on image data or on data used to then generate an image.

In one embodiment, the processor 22 includes the detector 18. Separate or the same components both detect intensities or other characteristic from or as the ultrasound data as well as process the data prior to or after detection.

The processor 22 is configured to maintain tongue information in the ultrasound data. Ultrasound data is data at any stage along the ultrasound pipeline, such as element data, beamformed data, pre-detected data, detected data (e.g., B-mode intensities), pre-scan converted data, scan converted data, or image data. The processor 22 maintains the tongue information by suppress signals from objects other than the tongue and/or suppressing noise in the ultrasound data. Alternatively or additionally, the tongue information may be replaced by a fit curve or model, generally maintaining tongue information while suppressing other information.

The processor 22 maintains the tongue information by performing one or more processing techniques on or with the ultrasound data. For example, the processor 22 is programmed to or is a filter for thresholding, persisting, high pass filtering, masking, segmenting, edge detecting, spatial compounding, template fitting, and/or frequency compounding.

The processor 22 generates an image from the processed information. Alternatively, the processor 22 controls generation of the image based on the processed information. The image is formatted in a display format and mapped to grey or color values for pixels.

The display 24 is a CRT, monitor, flat screen, LCD, projector or other display for displaying the tongue image. The display image format or display region is trapezoidal, trapezoidal like, rectangular, sector, pie shaped, Vector® or other shape. The image is updated in real-time, such as updating the image as each new frame of data is acquired.

The displayed image is of the tongue. The ultrasound data output by the processor 22 is used to generate the image. The processing results in the image having predominantly or more recognizable tongue information. A sequence of such images on the display shows motion of the tongue. An image of the sequence may be generated while the receive beamformer operates to scan for the next or subsequent frame of ultrasound data for generating another image in the real-time sequence.

The memory 26 is non-transitory device for storing data, such as a buffer, cache, RAM, removeable media, hard drive, magnetic, optical, or other now known or later developed memory. The memory 26 is a single device or group of two or more devices.

The memory 26 stores the ultrasound data. For example, the memory 26 stores flow (e.g., velocity, energy or both) and/or B-mode data. The stored data is used for transfer to and processing by the processor 22. Alternatively, the ultrasound data is transferred to the processor 22 from another device.

The memory 26 is additionally or alternatively a non-transitory computer readable storage medium with processing instructions. Data representing instructions executable by the programmed processor 22 for tongue imaging in medical diagnostic ultrasound is stored in the memory 26. The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

In the system of FIG. 4 or the method of FIG. 1, further features may be used for speech therapy. For example, video of the tongue moving and the audio of the subject trying to pronounce different words are both recorded. A given attempt, multiple attempts or an entire therapy session may be recorded, such as recording the video and audio over 15-30 minutes. The video and audio are synchronized. The therapist may then study any concerns, and/or the patient may review the work and feedback.

Automatic or manual placement of a marker on the image may be provided. The marker acts as a target for moving the tongue. The patient may move their tongue within their mouth to make the representation of the tongue on the image touch the marker. Multiple markers may be used.

Grooves or a tactile indicator of orientation of the transducer may be provided. The patient may be assisted in orienting the transducer while placed to scan their mouth as it may be a challenge to keep the smooth probe positioned correctly throughout the study. A strap or chin rest structure may alternatively be provided.

A reference library of images or video (sequence of images) may be provided for display. The reference images or video may show the correct positions or motion of the tongue for making different sounds. Synchronized audio may be stored as well. Representations of incorrect position or motion may also be shown to better indicate the difference or change needed to obtain the correct position or motion. The library may be used to help patients or to train speech pathologists.

A side-by-side display of a reference image or video (correct position and motion) and an image of the subject's tongue may be useful. Similarly, sequential or simultaneous display of the patient's tongue from different times may be useful. For example, images from previous session with the patient are recalled or displayed side-by-side with images from a current session. Differences may be highlighted manually or automatically.

A menu structure or text input system may be used for generating reports, such as a speech report. One or more images, such as video and audio, may be included with the report in an electronic format. Such a report may be generated for review by others for each session or as a collection of sessions.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for tongue imaging in medical diagnostic ultrasound, the method comprising:
   positioning an ultrasound transducer to scan a tongue of a patient;
   scanning the tongue of the patient with the ultrasound transducer;
   acquiring data from the scanning, the data representing a mouth, including the tongue, of the patient;
   processing the data, the processing increasing return of the tongue relative to other signals from anatomic structure of the mouth of the patient represented by the data;
   displaying a sequence of images of the tongue from the processed data, the sequence of images showing movement of the tongue.

2. The method of claim 1 wherein positioning comprises locating the transducer outside of the patient in contact with the skin below the mouth.

3. The method of claim 1 wherein scanning comprises sampling along one, two, or three-dimensions with ultrasound.

4. The method of claim 1 wherein acquiring comprises acquiring in real-time with the scanning.

5. The method of claim 1 wherein acquiring comprises acquiring the data from a memory after the scanning is complete.

6. The method of claim 1 wherein acquiring comprises acquiring B-mode data and wherein processing comprises applying a threshold to the B-mode data such that values of the data below the threshold are decreased.

7. The method of claim 1 wherein processing comprises persisting, spatial compounding, frequency compounding, or combinations thereof of multiple frames of the data from different times.

8. The method of claim 1 wherein processing comprises high pass filtering the data.

9. The method of claim 1 wherein processing comprises dividing the signals into low, middle, and high ranges of values, and decreasing the low and high ranges relative to the middle range.

10. The method of claim 1 wherein processing comprises edge detection.

11. The method of claim 1 wherein processing comprises performing two or more of:
   applying a threshold to B-mode data such that values of the data below the threshold are decreased;
   persisting;
   spatial compounding;
   frequency compounding;
   high pass filtering;
   unsharp masking; and
   edge detecting.

12. The method of claim 1 wherein displaying comprises displaying a one, two, or three-dimensional representation.

13. In a non-transitory computer readable storage medium having stored therein data representing instructions executable by a programmed processor for tongue imaging in medical diagnostic ultrasound, the storage medium comprising instructions for:
   obtaining ultrasound data representing a tongue;
   increasing, by image processing, a distinction between a surface of the tongue and other structure represented in the ultrasound data; and
   displaying an image of the surface of the tongue.

14. The non-transitory computer readable storage medium of claim 13 wherein obtaining comprises repetitively acquiring the ultrasound data in real-time with repetitive performance of the displaying, the repetitive performance of the displaying resulting in a sequence of images showing movement of the surface of the tongue.

15. The non-transitory computer readable storage medium of claim 13 wherein increasing by image processing comprises one or more of thresholding, persisting, high pass filtering, masking, segmenting, edge detecting, spatial compounding, or frequency compounding.

16. The non-transitory computer readable storage medium of claim 13 wherein obtaining comprises obtaining the ultrasound data representing two-dimensional region extending as a cross-section along a longitudinal axis of the tongue and wherein displaying comprises displaying the image as a patient speaks with the surface of the tongue shown in feedback to the patient.

17. A system for tongue imaging in medical diagnostic ultrasound, the system comprising:
   an ultrasound transducer;
   a receive beamformer operable to receive ultrasound data from a scan of a patient using the ultrasound transducer;
   an image processor configured to maintain tongue information in the ultrasound data and to suppress signals for structure other than the tongue information and to suppress noise in the ultrasound data; and
   a display operable to display an image of a tongue as a function of the ultrasound data output by the image processor.

18. The system of claim 17 wherein the image processor is configured to suppress and maintain by one or more of thresholding, persisting, high pass filtering, masking, segmenting, edge detecting, spatial compounding, or frequency compounding.

19. The system of claim 17 wherein the image processor is configured to detect intensities from the ultrasound data, the maintaining and suppressing being performed on the intensities.

20. The system of claim 17 wherein the display displays a sequence of images of the tongue, including the image of the tongue, while the receive beamformer operates.

* * * * *